United States Patent
Ho (10) Patent No.: US 11,313,540 B1
(45) Date of Patent: Apr. 26, 2022

(54) STERILIZATION DEVICE FOR IMPROVING DISINFECTION EFFECT

(71) Applicant: OXTI CORPORATION, New Taipei (TW)

(72) Inventor: Chih-Feng Ho, New Taipei (TW)

(73) Assignee: OXTI CORPORATION, New Taipei (TW)

( * ) Notice: Subject to any disclaimer, the term of this patent is extended or adjusted under 35 U.S.C. 154(b) by 0 days.

(21) Appl. No.: 17/232,155

(22) Filed: Apr. 16, 2021

(51) Int. Cl.
*F21V 17/10* (2006.01)
*F21V 33/00* (2006.01)
*A61L 9/20* (2006.01)

(52) U.S. Cl.
CPC ............... *F21V 17/10* (2013.01); *A61L 9/20* (2013.01); *F21V 33/006* (2013.01); *A61L 2209/15* (2013.01)

(58) Field of Classification Search
CPC ..... F21V 17/10; F21V 33/006; A61L 2209/15
See application file for complete search history.

(56) References Cited

U.S. PATENT DOCUMENTS

| | | | |
|---|---|---|---|
| 2014/0170019 A1* | 6/2014 | Gil | A61L 2/10 422/24 |
| 2015/0086420 A1* | 3/2015 | Trapani | A61L 9/015 422/24 |

* cited by examiner

*Primary Examiner* — Anabel Ton
(74) *Attorney, Agent, or Firm* — Leong C. Lei (57) ABSTRACT

A sterilization device for improving a disinfection effect includes: a main body, including a first surface, a second surface opposite to the first surface, and an accommodating hole, two sides of the main body respectively configured with a through hole, and the through holes in communication with the accommodating hole; a sanitizing lamp, configured on the second surface of the main body, the sanitizing lamp including a lighting element, sensor element, control element and power element; and a fixing member, passed through the through holes and accommodating hole of the main body. Taking a door handle as an example, the main body is passed through with the door handle through the accommodation hole, and the fixing member is then inserted through the through holes and accommodating hole, thereby fixing the main body on the door handle. Thus, the sanitizing lamp emits light to disinfect the door handle.

4 Claims, 9 Drawing Sheets

STERILIZATION DEVICE FOR IMPROVING DISINFECTION EFFECT

(a) TECHNICAL FIELD OF THE INVENTION

The present invention relates to a sterilization device, and more particularly to a sterilization device for improving a disinfection effect.

(b) DESCRIPTION OF THE PRIOR ART

In the past, infectious diseases have changed the human history many times, and infectious diseases are one of the causes of most deaths in the world. With the change of human life style, the global climate change changes the transmission route and distribution area of infectious diseases; viruses and pathogenic microorganisms continue to adapt and mutate, causing every kind of emerging infectious diseases and re-emerging infectious diseases to happen incessantly; from early measles, smallpox, malaria, influenza to the recent severe acute respiratory syndrome (SARS), new type A influenza virus (H1N1), Middle East respiratory syndrome (MERS-CoV) and new coronavirus pneumonia (COVID-19), the currently known infectious transmission of such infectious diseases is mainly spread by direct contact with viral secretions or droplets.

Patients cause viruses to attach to doorknobs or door handles due to coughing, sneezing or contact with respiratory secretions, such that the doorknobs or door handles are highly contagious routes of the viruses. Taiwan Patent NO. M480983, titled "Door handle disinfection device", discloses a disinfection device including a door panel and disinfection pot, where the disinfection pot is used to spray disinfectant onto a door handle.

However, the disinfectant is corrosive, irritating to skin, and has a bleaching effect and irritating odor harmful to human. In addition, one side of the door panel needs to be opened with a room, inside which the sprayer of the disinfection device is installed, where one end of the sprayer is embedded with the disinfection pot filled with disinfectant, such that the original door panel is destroyed, and the room is not easy to be opened on the door panel if it is made of metal.

SUMMARY OF THE INVENTION

To overcome the above disadvantages, the present invention proposes a sterilization device for improving a disinfection effect, including: a main body, including a first surface, a second surface opposite to the first surface, and an accommodating hole, two sides of the main body respectively configured with a through hole, and the through holes in communication with the accommodating hole; a sanitizing lamp, configured on the second surface of the main body, the sanitizing lamp including a lighting element, sensor element, control element and power element; and a fixing member, passed through the through holes and accommodating hole of the main body.

Preferably, the first surface of the main body is configured with a transparent area.

Preferably, the main body is configured with a power switch.

Preferably, the sanitizing lamp includes a reception element, and the reception element is a wireless signal receiver.

Preferably, the fixing part is an elastic fastening belt.

Taking a door handle as an example, the main body is passed through with the door handle through the accommodation hole, and the fixing member is then inserted through the through holes and the accommodating hole, thereby fixing the main body on the door handle with fixing member. Thus, the sanitizing lamp emits light to illuminate the door handle to disinfect it. Furthermore, the sensor element detects around the door handle, and the control element will control the sanitizing lamp to stop emitting light when someone approaching is sensed.

DETAILED DESCRIPTION OF THE PREFERRED EMBODIMENTS

Figure 1:
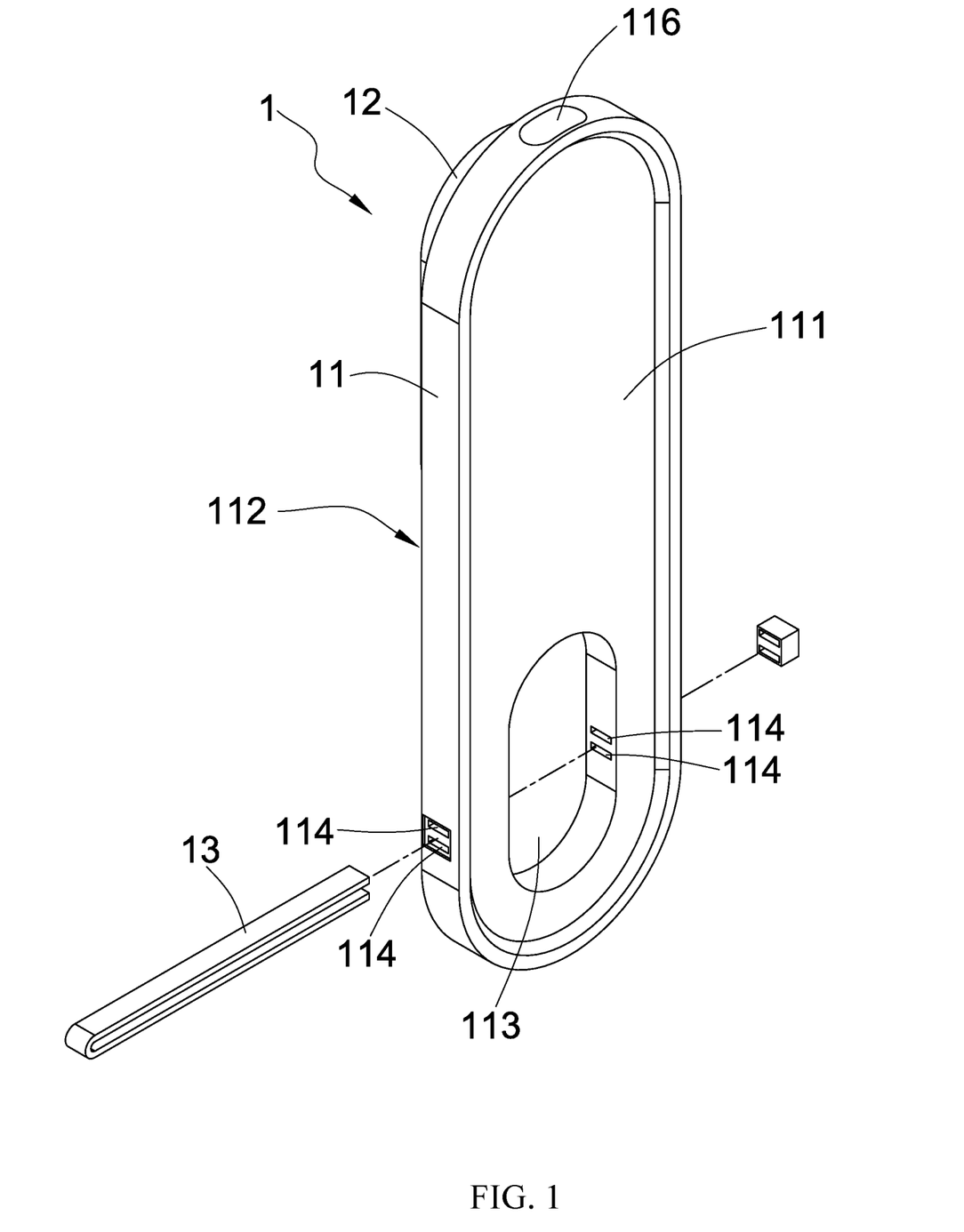
FIG. 1 is a schematically perspective view of a sterilization device for improving disinfection effect of the present invention.

Referring to FIG. 1, a sterilization device 1 for improving a disinfection effect of the present invention includes a main body 11, a sanitizing lamp 12 and a fixing member 13.

Figure 2:
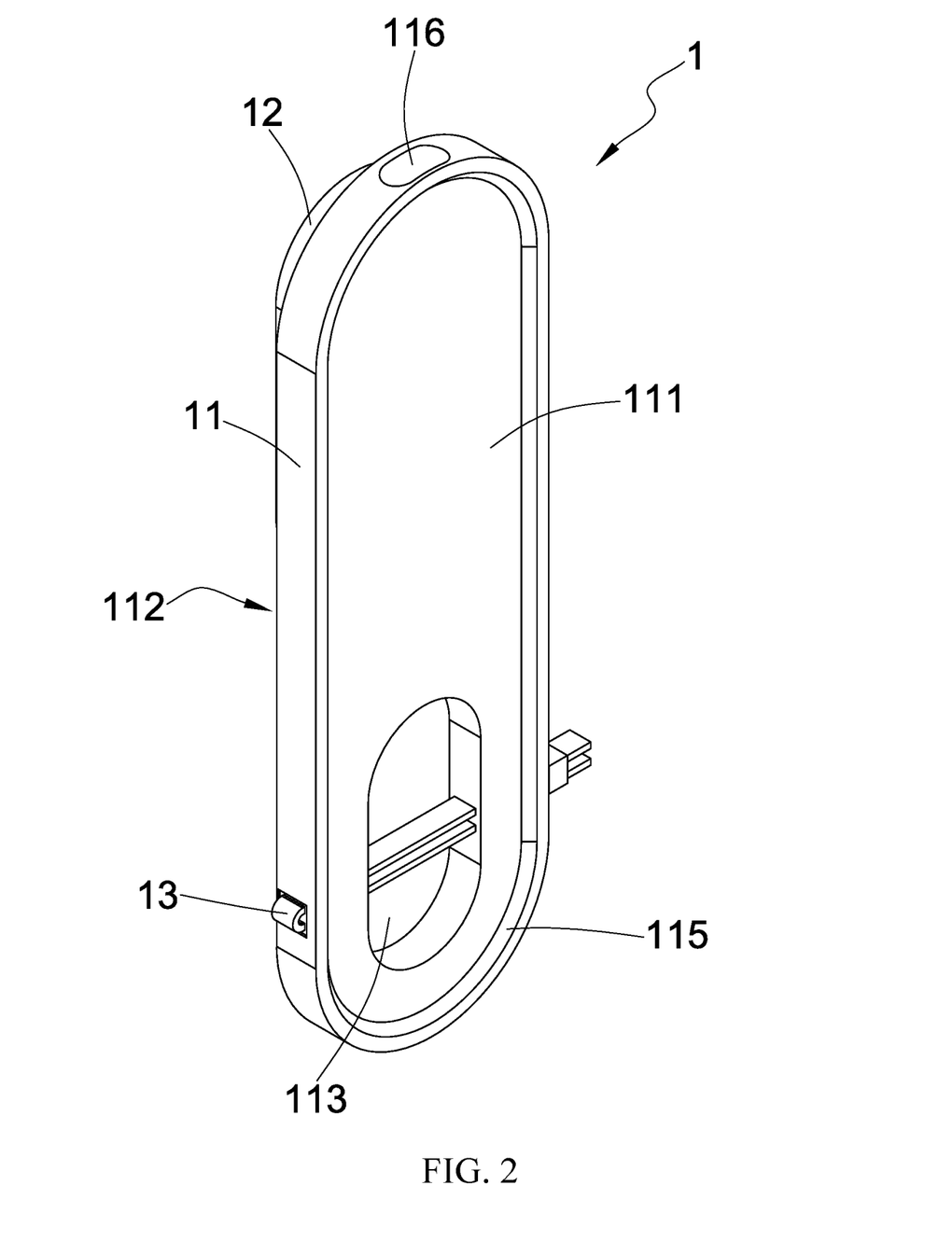
FIG. 2 is a perspective view of the present invention, where a fixing member is inserted through the through holes and an accommodating hole of a main body.

Referring to FIG. 2, the main body 1 includes a first surface 111, a second surface 112 opposite to the first surface 111, and an accommodating hole 113, where the accommodating hole 113 may be a long hole, but the present invention is not so limited. The two lateral sides of the main body 11 are respectively configured with two through holes 114 in communication with the accommodating hole 113. The first surface 111 of the main body 11 may further be configured with a transparent area 115, which may be made of a transparent material and allows light to pass through. One side of the main body 11 is further configured with a power switch 116.

Figure 3:
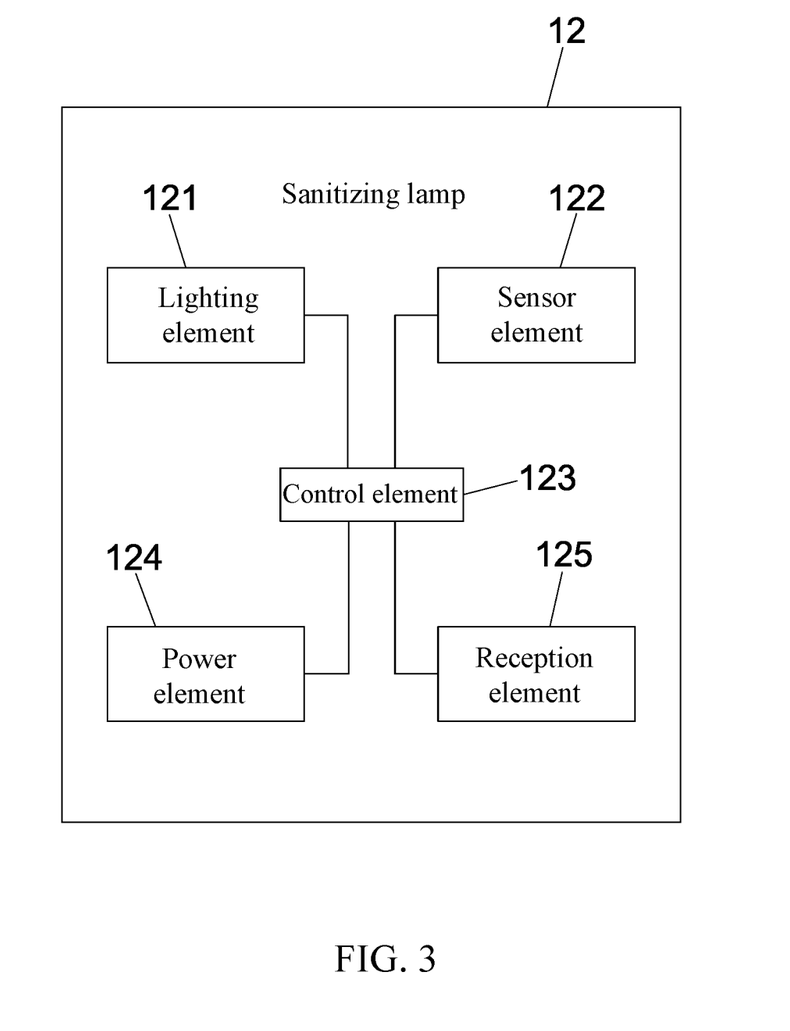
FIG. 3 is a block diagram of a sanitizing lamp.

Referring to FIG. 3, the second surface 112 of the main body 11 is configured with the sanitizing lamp 12 including a lighting element 121, a sensor element 122, a control element 123, a power element 124 and a reception element 125. The sanitizing lamp 12 is used to emit light for disinfection such as ultraviolet light. The lighting element 121 is used as the light source of the sanitizing lamp 12 and may be a UV-B ultraviolet lamp, a UV-C violet lamp, a mercury lamp, a metal halide lamp or a xenon lamp, but the present invention is not so limited. The sensor element 122 is used to sense a human body (shown in FIG. 9) and may be an infrared sensor element, a light sensor element, a ultrasonic sensor element or a thermal sensor element. The control element 123 is used to control the lighting element 121, and the power element 124 provides electric power; the power element 125 may for example be a battery. The power switch 116 of the main body 11 is in electric connection with the power element 123 of the sanitizing lamp 12. The reception element 125 is used to receive a wireless signal and may for example be a wireless signal receiver, allowing the control element 123 to control the lighting element 121 to emit light according to the wireless signal. For example, a smart phone or remote controller may be used to emit the wireless signal to the reception element 125.

The fixing member 13 is inserted through the through holes 114 of the main body 11 and the accommodating hole 113, and may be an elastic fastening belt, but the present invention is not so limited.

Figure 4:
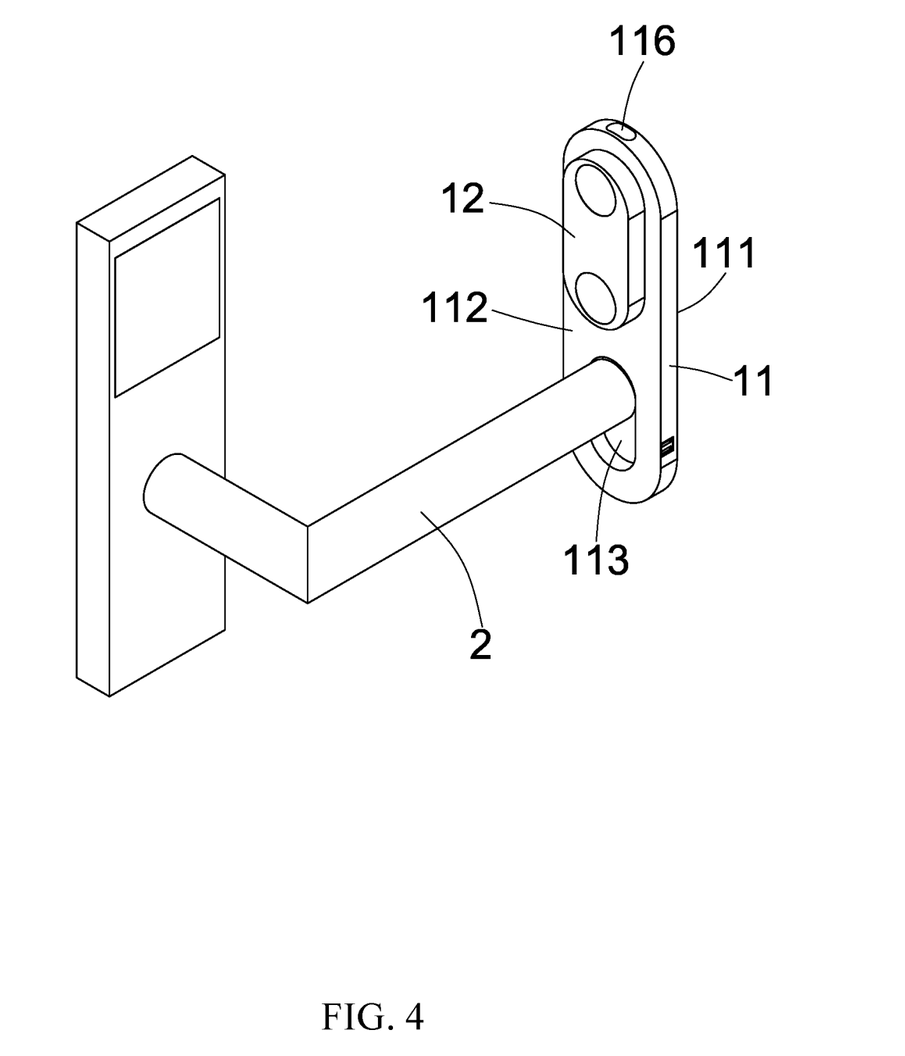
FIG. 4 shows the accommodation hole of the main body being passed through with a door handle.
Figure 5:
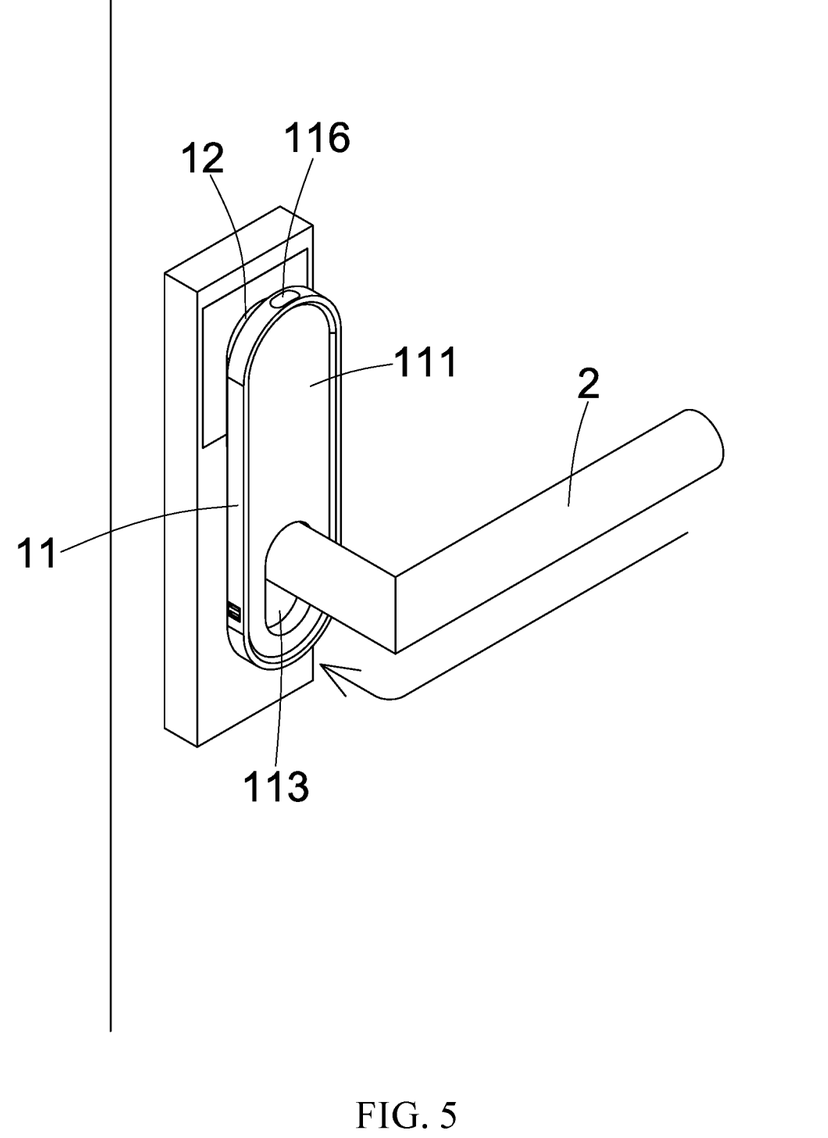
FIG. 5 shows the accommodation of the main body being placed on the door handle.
Figure 6:
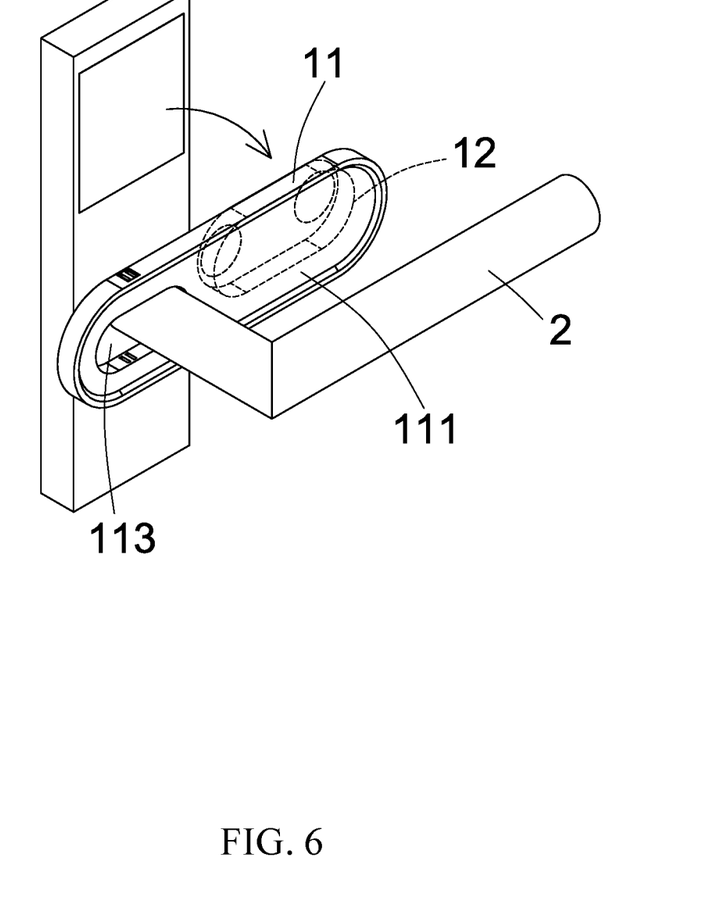
FIG. 6 shows the main body being adjusted in a direction allowing the sanitizing lamp to illuminate the door handle.
Figure 7:
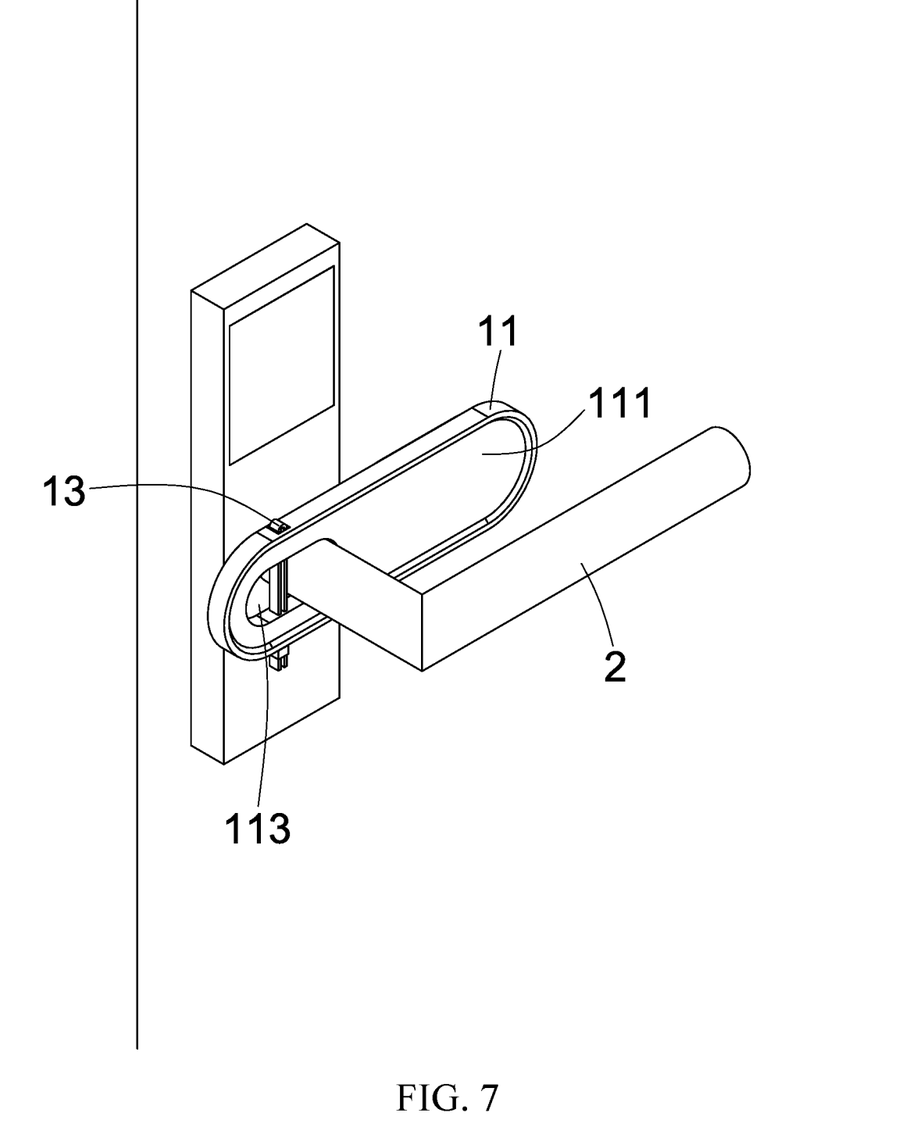
FIG. 7 shows the fixing member being passed through the through holes and accommodating hole of the main body to fix the main body on the door handle.
Figure 8:
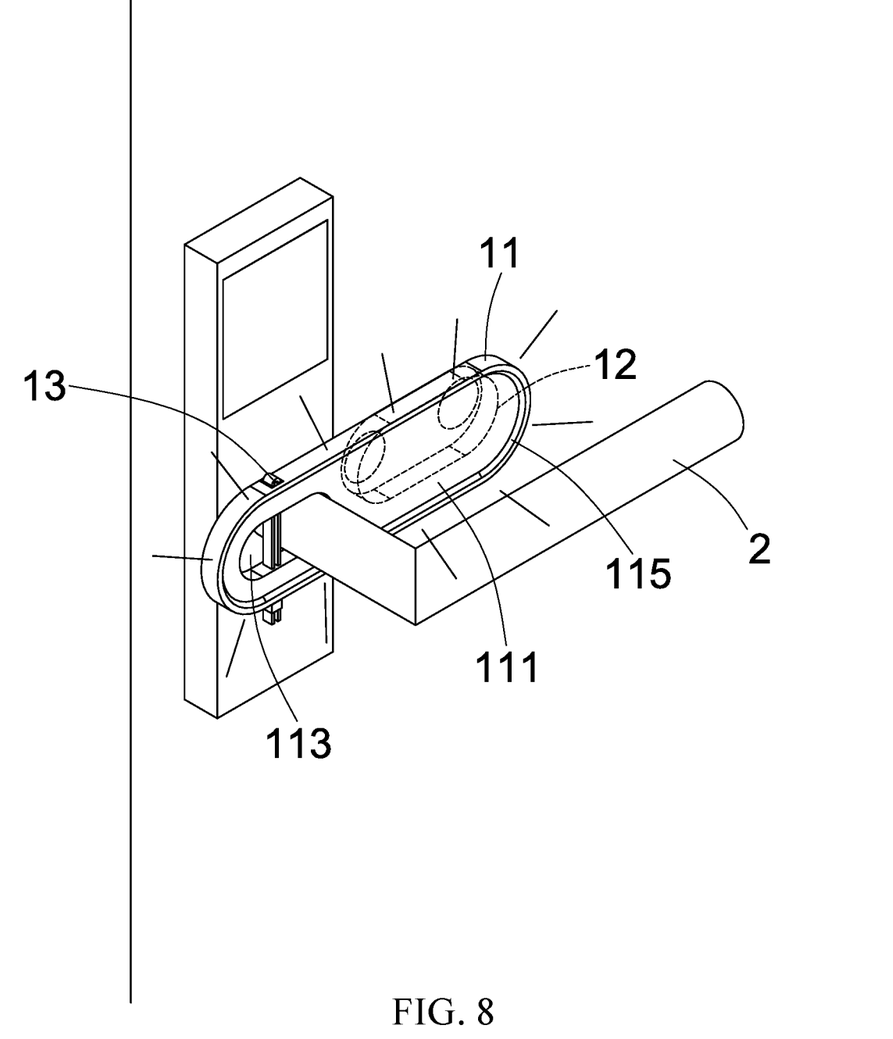
FIG. 8 shows the sanitizing lamp emitting light to illuminate the door handle.
Figure 9:
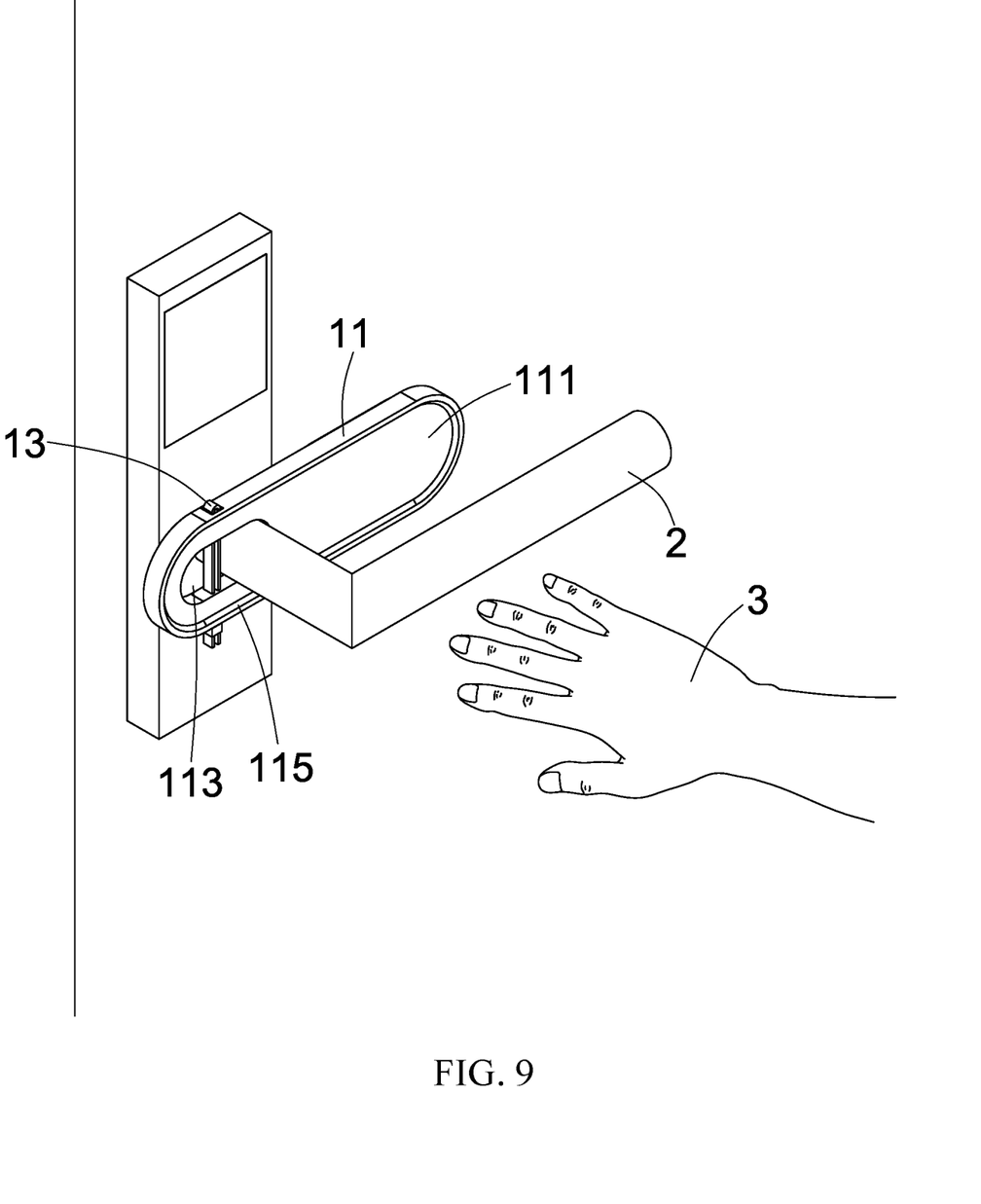
FIG. 9 shows the sanitizing lamp stopping emitting light when someone approaches.

Referring to FIGS. 4 and 5, taking a door handle 2 as an example, the main body 11 is passed through with the door handle 2 through the accommodating hole 113, where the first surface 111 of the main body 11 faces outward, and the second surface 112 of the main body 11 faces inward, allowing the sanitizing lamp 12 of the second surface 112 to hide inside the main body 11, thereby being protected by the main body 11 without being easily damaged by external force. Referring to FIG. 6, the direction or position of the main body 1 is adjusted again, allowing the sanitizing lamp 12 to illuminate the door handle 2. Referring to FIGS. 1 and 7, the fixing member 13 is further passed through the through holes 114 of the main body 11 and the accommodating hole 113, so that the fixing member 13 fixes the main body 11 on the door handle 2. For example, the fixing member 13 is a fastening belt, such that the door handle 2 is fastened by the elasticity of the tightened fastening belt. Referring to FIG. 8, the sanitizing lamp 12 emits light to illuminate the door handle 2 to disinfect it. Referring to FIGS. 3 and 9, the sensor element 122 is further used to detect around the door handle 2; when a human body 3 is sensed approaching, the sensor element 122 will notify the control element 123, and the control element 123 then control the sanitizing lamp 12 to stop emitting light, avoiding harming a human body 3.

Conclusively, the sterilization device 1 for improving disinfection effect will not damage a door panel and can be apply on a door handle 2 with the simple operation of the device, being very convenient. Upon the detachment of the device 1, only the fixing part 13 needs to be removed. In addition, the fixing part 13 may for example be a fastening belt made of plastic such that the device 1 can be detached with a sharp object such as scissors, being simple and easy in operation. The ultraviolet sterilization of the present invention has a better effect than a disinfectant sterilization. In addition, the present invention has both sensing and remote-control effects.

I claim:

1. A sterilization device for improving a disinfection effect, comprising:
    a main body, comprising a first surface, a second surface opposite to said first surface, and an accommodating hole, two lateral sides of said main body respectively configured with two through holes, and said through holes being in communication with said accommodating hole;
    a sanitizing lamp, configured on said second surface of said main body, said sanitizing lamp comprising a lighting element, a sensor element, a control element and a power element; and
    a fixing member inserted through said through holes and accommodating hole of said main body, thereby enabling said main body to be fixed on a door handle;
    wherein said fixing member is an elastic fastening belt.

2. The device according to claim 1, wherein said first surface of said main body is configured with a transparent area.

3. The device according to claim 1, wherein said main body is configured with a power switch.

4. The device according to claim 1, wherein
    said sanitizing lamp further comprises a reception element, and said reception element is a wireless signal receiver.

\* \* \* \* \*